Figure 1:
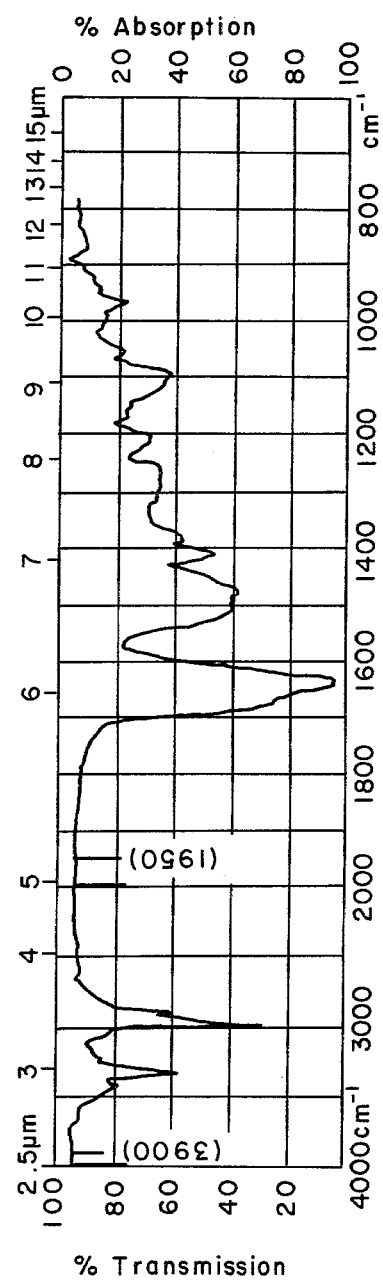

United States Patent

Traber et al.

[11] 4,288,431
[45] Sep. 8, 1981

[54] CYCLOSPORIN DERIVATIVES, THEIR PRODUCTION AND PHARMACEUTICAL COMPOSITIONS CONTAINING THEM

[75] Inventors: Rene P. Traber, Basel; Hans Hofmann, Ettingen; Eugen Härri, Therwil; Kuhn Max, Basel, all of Switzerland

[73] Assignee: Sandoz Ltd., Basel, Switzerland

[21] Appl. No.: 84,100

[22] Filed: Oct. 12, 1979

[30] Foreign Application Priority Data

Oct. 18, 1978 [CH] Switzerland ............... 10776/78
Mar. 22, 1979 [CH] Switzerland ............... 2696/79
Aug. 15, 1979 [CH] Switzerland ............... 7480/79

[51] Int. Cl.³ ............... A61K 37/00; C07C 103/52; C12P 21/04
[52] U.S. Cl. ............... 424/177; 260/112.5 R; 435/71
[58] Field of Search ............... 424/177; 260/112.5 R; 435/71

[56] References Cited

U.S. PATENT DOCUMENTS 4,108,985 8/1978 Rüegger et al. ............... 424/177

OTHER PUBLICATIONS

Traber, et al., Chem. Abstr. 87, 1977 80949A.

*Primary Examiner*—Delbert R. Phillips
*Attorney, Agent, or Firm*—Gerald D. Sharkin; Robert S. Honor; Thomas O. McGovern

[57] ABSTRACT

Compounds of formula I

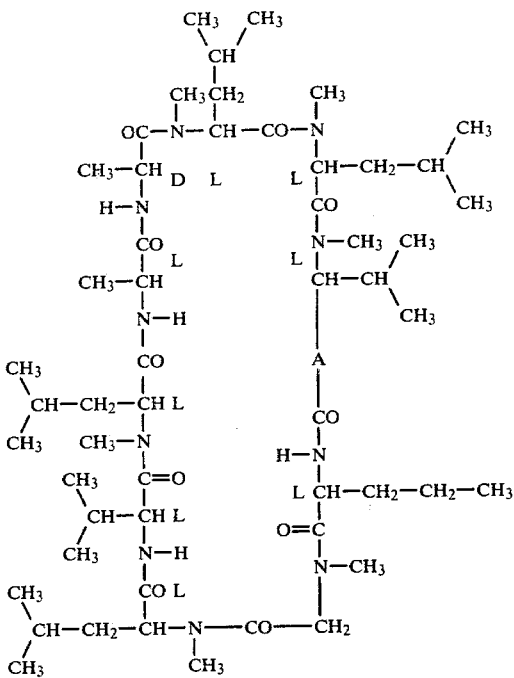

selected from the group consisting of cyclosporin G, wherein A is

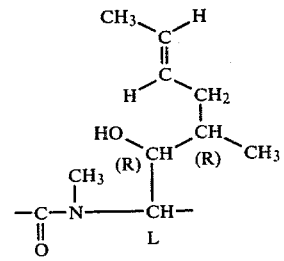

dihydrocyclosporin G, wherein A is

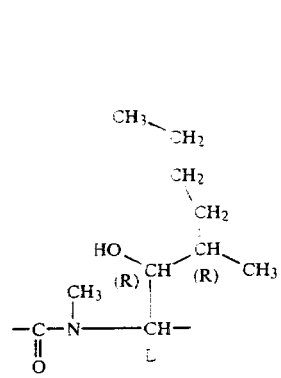
and isocyclosporin G, wherein A is
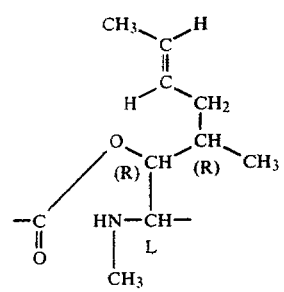
are useful in treating inflammations and arthritis and as immuno-suppressant agents.
9 Claims, 6 Drawing Figures

CYCLOSPORIN DERIVATIVES, THEIR PRODUCTION AND PHARMACEUTICAL COMPOSITIONS CONTAINING THEM

This invention relates to cyclosporin derivatives, which are monocyclic unadecapeptide derivatives, their production and pharmaceutical compositions containing them.

The present invention provides cyclosporin G, dihydrocyclosporin G or isocyclosporin G of formula I The present invention provides a process for the production of cyclosporin G, dihydrocyclosporin G or isocyclosporin G which comprises, (a) for the production of cyclosporin G, cultivating a cyclosporin G-producing strain of the fungal species Tolypocladium in the presence of a nutrient medium and isolating cyclosporin G, (b) for the production of dihydrocyclosporin G, reducing cyclosporin G, or (c) for the production of iso-cyclosporin G, rearranging cyclosporin G.

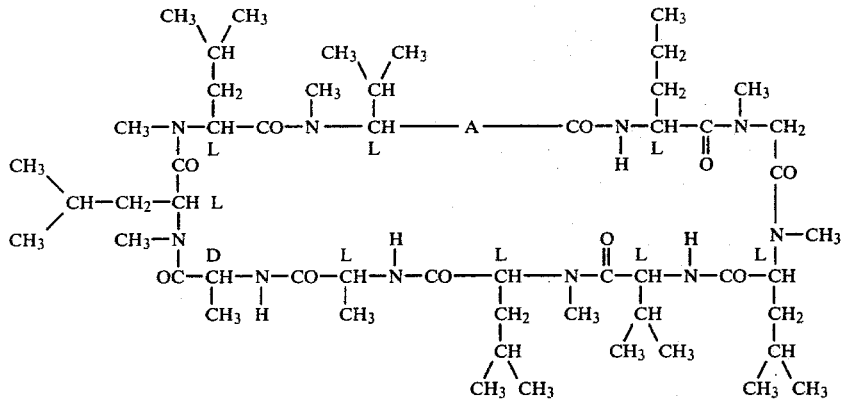

wherein A is

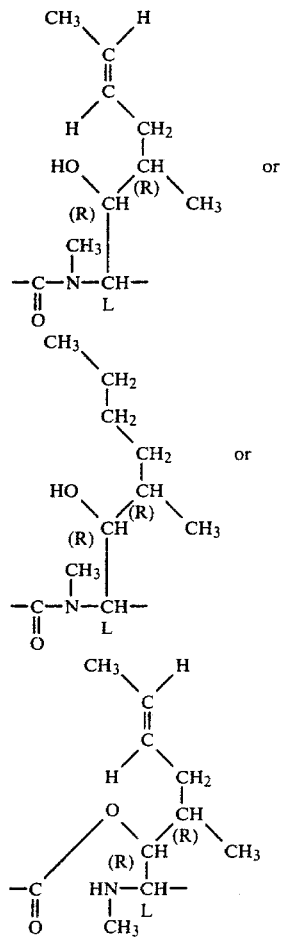

respectively.

The cultivation according to process (a) may be effected in known manner for the cultivation of analogous strains, e.g. as described in Example 1.

A preferred cyclosporin G producing strain is a strain of *Tolypocladium inflatum* Gams. A preferred strain is freely available and has been described in U.K. Pat. No. 1,451,509. This has been deposited with the U.S. Department of Agriculture (Northern Research and Development Division), Peoria, Ill., U.S.A. under the code NRRL 8044 as well as with the Fermentation Research Institute of Japan Inage, Chiba City, Japan, under the code FERM P No 2796. This strain was formerly classed as *Trichoderma polysporium* (Link ex Pers) and has now been reclassified as a *Tolypocladium inflatum* Gams strain.

Other cyclosporin G-producing strains of *Tolypocladium inflatum* Gams may be produced e.g. by selection, mutation of the above mentioned preferred strain under the influence of ultra-violet or x-ray radiation, or reaction of this strain with appropriate chemicals.

Cyclosporin G may be isolated in known manner for isolating fermentation products, e.g. as described in Example 1, from the culture broth. The purification conditions should be chosen to separate cyclosporin G from other natural products that may be present, e.g. the less polar cyclosporin D, and the more polar cyclosporins A and B (also known as S 7481/F-1 and S 7481/F-2 respectively) as well as the yet more polar cyclosporin C.

Process (b) may be effected using conventional reduction processes, e.g. catalytic hydrogenation.

Suitable solvents include ethyl acetate or lower alkanols such as methanol, ethanol or isopropanol. Conveniently neutral conditions are used. Suitable reaction temperatures are from 20° to 30° C. at atmospheric pressure or at a slightly elevated pressure. Suitable catalysts include platinium or preferably palladium, e.g. palladium-on-charcoal.

Process (c) may be effected in conventional manner for the rearrangement of analogous cyclosporins, e.g. under acid conditions. Conveniently a strong organic acid is used, e.g. trifluoroacetic acid, methanesulphonic acid or p-toluenesulphonic acid.

The amount of strong acid present is conveniently from 1 to 4 moles per mole of cyclosporin G.

As solvent may be used, for example, methanol, chloroform or dioxane. Reaction temperatures are conveniently from 20° to 65° C. and preferably from 45° to 55° C.

In the following Examples, all temperatures are in degrees centigrade and are uncorrected. All ratios are in parts by volume unless stated otherwise. Silicagel is e.g. silicagel 60 (Merck; partitale size 0.063–0.2 mm).

EXAMPLE 1

Cyclosporin G

500 Liters of a nutrient solution (containing per liter 40 g glucose, 2 g sodium caesinate, 2.5 g ammonium phosphate, 5 g $MgSO_4.7H_2O$, 2 g $KH_2PO_4$, 3 g $NaNO_3$, 0.5 g KCl, 0.01 g $FeSO_4$ and demineralized water to 1 liter) are innoculated with 50 liters of a preculture of the strain NRRL 8044 and incubated in a steel fermenter under stirring (170 r.p.m.) and under aeration (1 liter air/minute/liter nutrient solution) for 13 days at 27° (see also the above-mentioned U.K. patent specification).

The culture broth is stirred with the same volume of n-butyl acetate. The organic layer is separated, concentrated in a vacuum and partitioned between methanol/water (9:1) and petroleum ether. The methanolic phase is shaken with petroleum ether twice more to remove further fatty material. The methanolic phase is concentrated in a vacuum and water is added to precipitate the product which is filtered off. The product is chromatographed on a 5 to 7 fold amount of Sephadex LH 20 with methanol as eluant. The leading fractions are then chromatographed on silicagel using hexane/acetone (2:1) as eluant, affording first fractions containing mainly cyclosporins A and D (as well as some cyclosporin G) and then fractions containing cyclosporin C.

The first fractions are each treated with a 2 to 2.5 fold volume of acetone and at −15° crystals are produced. The crystals are chromatographed twice on silicagel using hexane/acetone (2:1) as eluant, yielding first fractions containing cyclosporin D (as well as some cyclosporin G). These fractions are dissolved in a 2 fold volume of acetone and allowed to crystallize at −15°. The crystals are crude cyclosporin D. The mother liquor contains, besides cyclosporin D, cyclosporin G and is concentrated to dryness. The residue is chromatographed on silicagel using water-saturated ethyl acetate as eluant. After cyclosporin D is eluted, further fractions contain cyclosporin G, which are chromatographed on silicagel first using chloroform/methanol (98:2) as eluant and then, for separation, hexane/acetone (2:1). The later fractions contain cyclosporin G in purified form which is crystallised twice from ether/petroleum ether (1:1) at room temperature. The final product is homogeneous by thin layer chromatography, >95% pure and comprises colourless polyhedrons of m.pt. 193°–194° (after drying of the crystals at 80° in a high vacuum for 2 hours).

$$[\alpha]_D^{20} = -245° \ (c = 1 \text{ in } CHCl_3)$$
$$= -191° \ (c = 1.04 \text{ in } CH_3OH)$$

Figure 2:
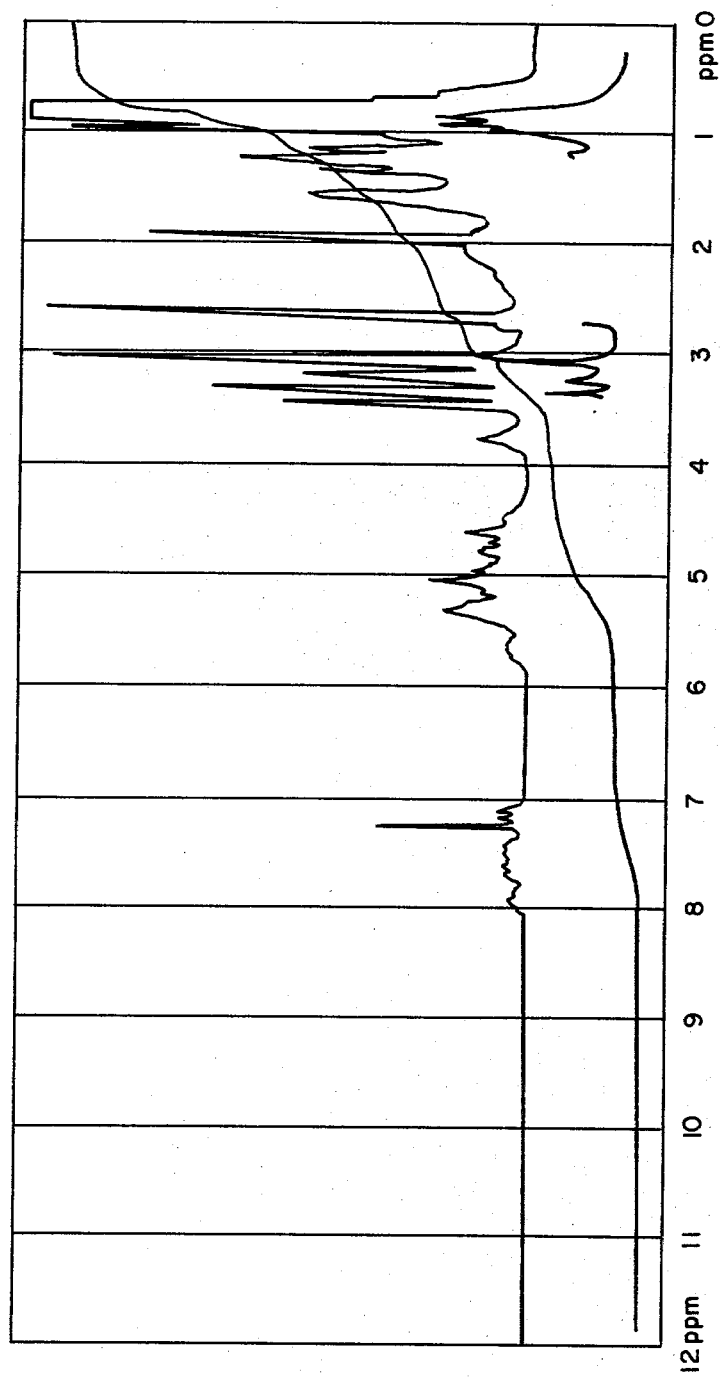

UV spectrum in $CH_3OH$: end absorption
IR spectrum in $CH_2Cl_2$: see FIG. 1
IH.N.M.R. spectrum in $CDCl_3$ 90 $MH_z$ (Tetramethylsilane as internal standard): see FIG. 2
Formula: $C_{63}H_{113}N_{11}O_{12}$.

EXAMPLE 2

Dihydrocyclosporin G 700 mg palladium/charcoal (10% w/w Palladium) are hydrogenated in 20 ml ethanol over 30 minutes. A solution of 4.55 g cyclosporin G in 60 ml ethanol is added. The mixture is hydrogenated at 21° and at a pressure of 742 mm Hg until hydrogen uptake is complete. The catalyst is filtered off and the filtrate evaporated in a vacuum at 20° to 40° to dryness. The residue, dihydrocyclosporin G, is t.l.c and is obtained in the form of a white amorphous powder. M.pt. 150°–153° (after drying in a high vacuum at 80° for 4 hours).

Figure 3:
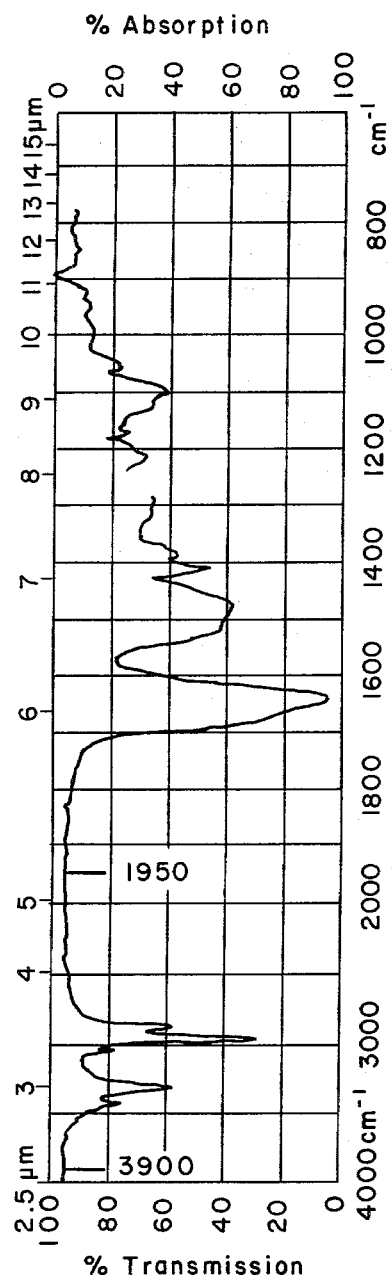
Figure 4:
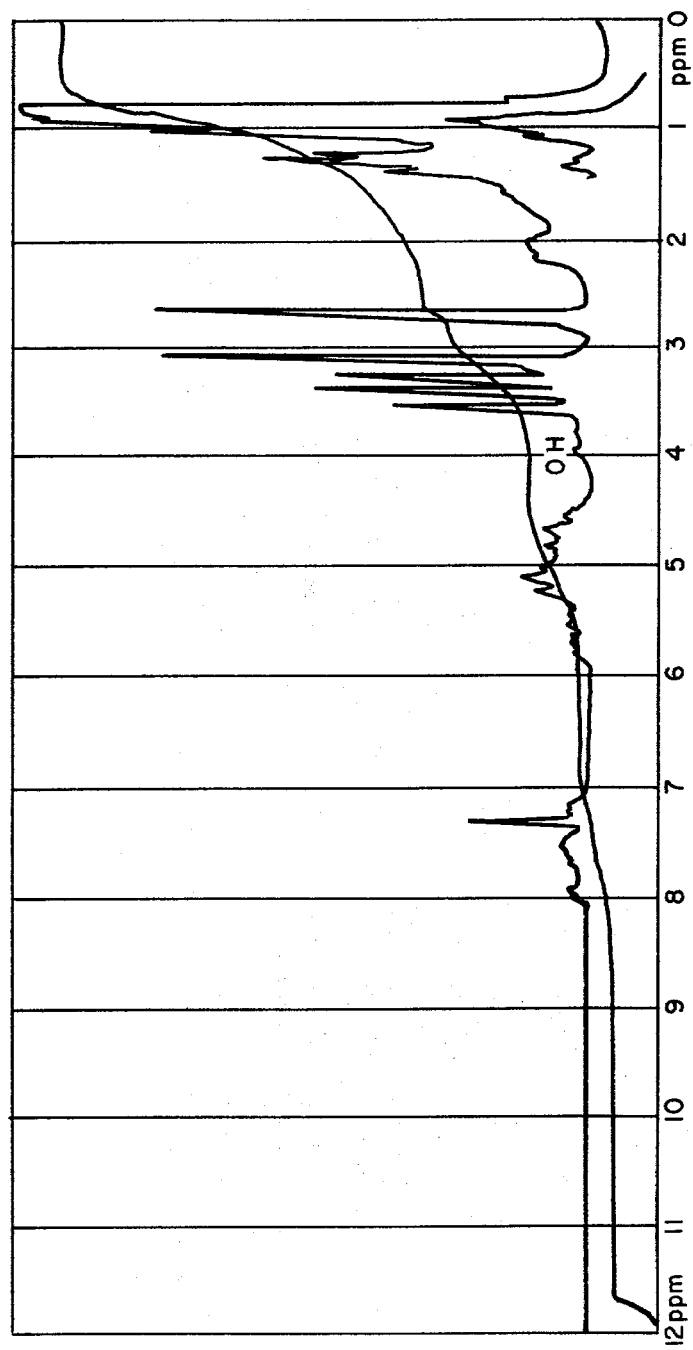

$[\alpha]_D^{20} = -232°$ (c=0.64 in $CHCl_3$)
UV spectrum in $CH_3OH$: end absorption
IR spectrum in $CH_2Cl_2$: see FIG. 3
IH.N.M.R. spectrum in $CDCl_3$ 90 $MH_z$ (Tetramethylsilane as internal standard): see FIG. 4
Formula: $C_{63}H_{115}N_{11}O_{12}$.

EXAMPLE 3

Iso-Cyclosporin G

A solution of 1.21 g methanesulphonic acid in 20 ml anhydrous dioxane is added to a solution of 6.08 g cyclosporin G in 40 ml anhydrous dioxane, and maintained at 50° under anhydrous conditions. The progress of the rearrangement is followed by thin layer chromatography on silicagel [Polygram SIL G foil CHCl₃/CH₃OH/ethylacetate 90:6:4; detection by iodine]. After 16 hours the mixture is cooled to room temperature. 1.13 g anhydrous sodium acetate are added to neutralise the acid. After 45 minutes, the mixture is filtered and the filtrate evaporated in a vacuum at 45°. The 8.1 g residue is chromatographed on 500 g silicagel using as eluant CHCl₃/CH₃OH (98:2). The fractions containing practically pure isocyclosporin G are combined, evaporated to dryness at 50° in a vacuum and the residue crystallised from ether at +7° to give the title compound m.pt. 143°–146°.

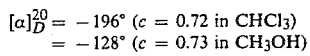
$$[\alpha]_D^{20} = -196° \ (c = 0.72 \text{ in } CHCl_3)$$
$$= -128° \ (c = 0.73 \text{ in } CH_3OH)$$

Figure 5:
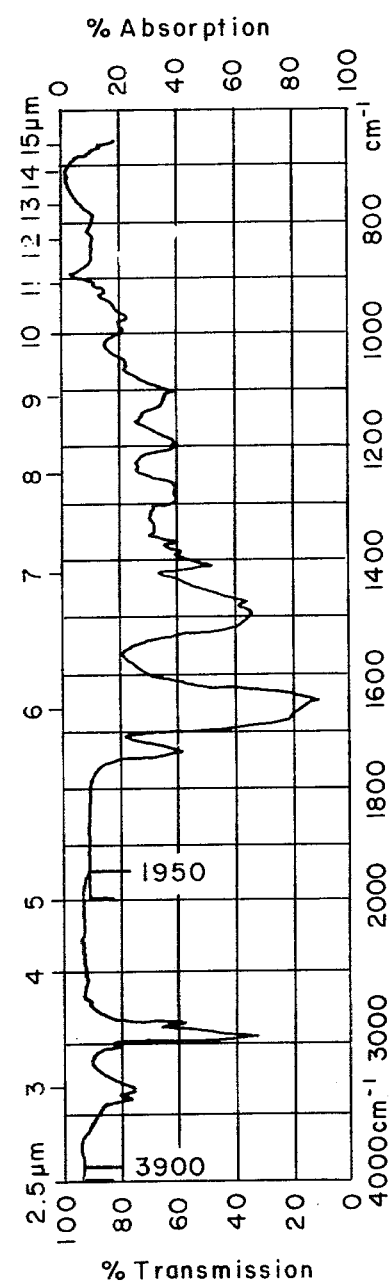
Figure 6:
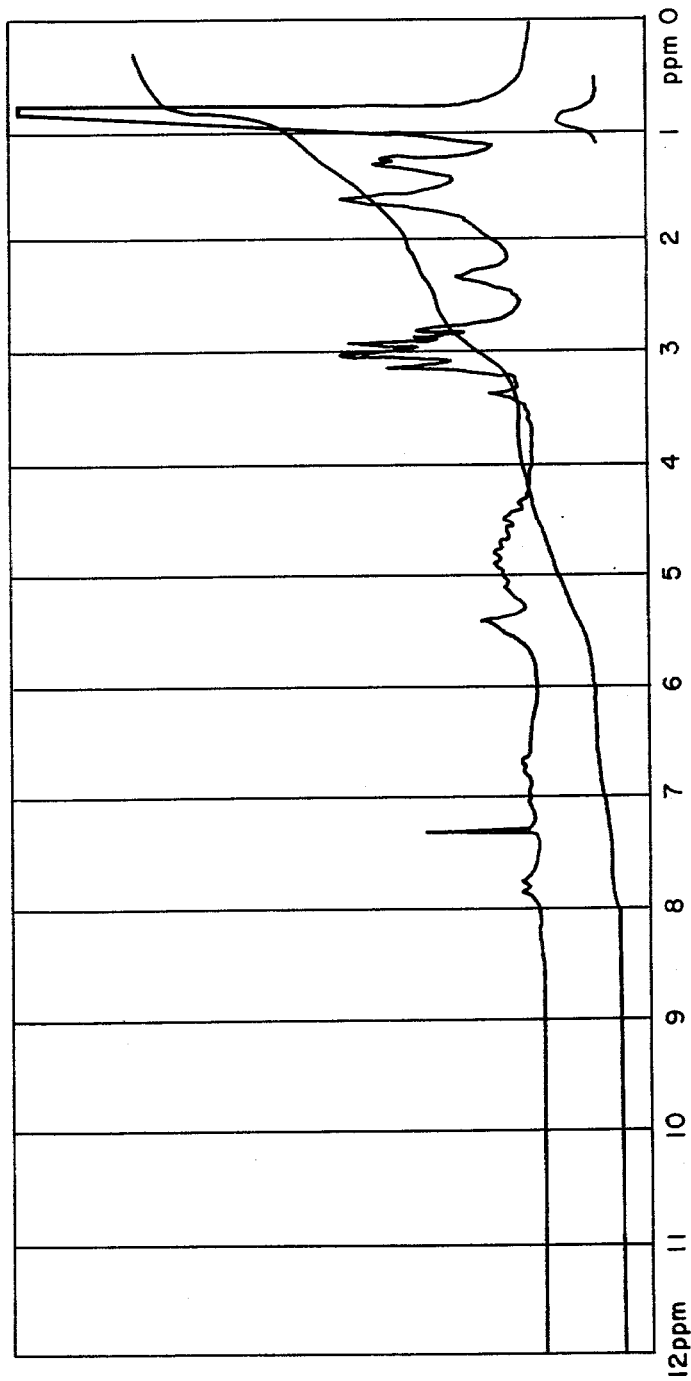

UV spectrum in CH₃OH: end absorption
IR spectrum in CH₂Cl₂: see FIG. 5
IH.N.M.R. spectrum in CDCl₃ 90 MHz (Tetramethylsilane as internal standard): see FIG. 6.

The compounds of formula I exhibit pharmacological activity. In particular the compounds exhibit anti-inflamatory activity and anti-arthritic activity as indicated by an inhibition of swellings in the Freunds adjuvant arthritis test in rats on p.o. administration of 30 to 100 mg/kg of the compounds.

The compounds are therefore useful for the treatment and prophylaxis of chronic inflammations, e.g. arthritis and rheumatic disorders.

Furthermore, the compounds exhibit immuno-suppressive activity, e.g. by their effect on humonal and cellular immunity, as indicated in standard tests, e.g.

(a) in the lymphocyte stimulation test according to Janossy in vitro at concentrations of 0.01 to 10.0 µg/ml a strong inhibition of H³-thymidine incorporation, of the proliferation rate and of the blastogenese of mice spleen lymphocytes stimulated with Concanavalin A was ascertained.

(b) Oxazolone test in mice:
A decrease in the ear swelling is observed upon administration of 5×70 mg/kg p.o. of the compounds.

(c) A local hemolysis in gel: Jerne test [J. F. Borel, Agents and Actions (1974) 4 p.277]. The inhibition of hemolytic plaque-forming cells, immunoglobulin antibodies and immunoglobulin G₂ₐ antibodies is observed at a dose of 3×50 mg/kg.

The compounds are therefore useful for the treatment autoimmune diseases.

For all these uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 900 mg, e.g. 300 to 900 mg, and dosage forms suitable for oral administration comprise from about 12 mg to about 450 mg (e.g. 25 to 300 or 150 to 300 mg) of the compounds admixed with a solid or liquid pharmaceutical carrier or diluent.

The present invention also provides a pharmaceutical composition comprising a compound of formula I in association with a pharmaceutical carrier or diluent.

Such compositions may be in the form of, for example, a solution or a tablet.

The preferred activity is the immunosuppressant activity.

The compound of Example 2 exhibits especially interesting activity.

What we claim is:
1. A compound of formula I

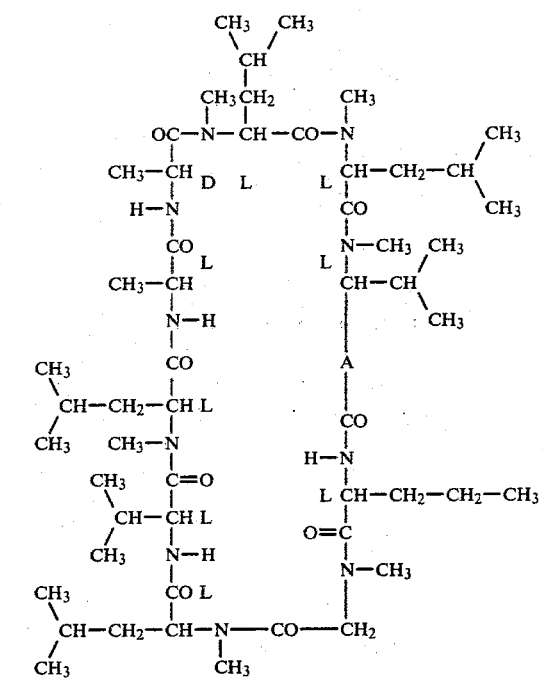

selected from the group consisting of cyclosporin G, wherein A is

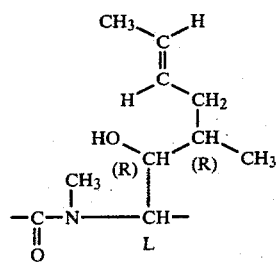

dihydrocyclosporin G, wherein A is

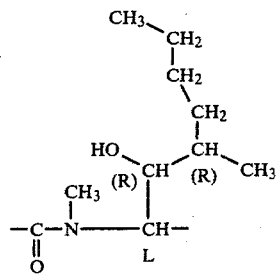

and isocyclosporin G, wherein A is

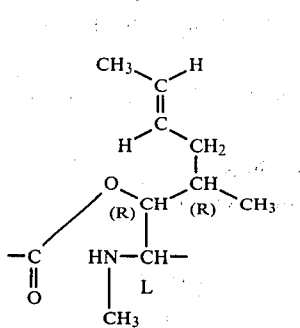

2. The compound of claim 1 which is cyclosporin G which has the following approximate characteristics:

$[\alpha]_D^{20} = -245°$ ($c = 1$ in $CHCl_3$)
$= -191°$ ($c = 1.04$ in $CH_3OH$)

UV spectrum in $CH_3OH$: end absorption
IR spectrum in $CH_2Cl_2$: see FIG. 1
IH.N.M.R. spectrum in $CDCl_3$ 90 MH$_z$ (Tetramethylsilane as internal standard): see FIG. 2
Formula: $C_{63}H_{113}N_{11}O_{12}$
and when in crystalline form a m.pt. of about 193°–194° C., and being more polar than cyclosporin D and less polar than cyclosporin A.

3. The compound of claim 1 which is cyclosporin G substantially free from cyclosporin D.

4. The compound of claim 1 which is cyclosporin G in greater than 95% purity.

5. The compound of claim 1 which is dihydrocyclosporin G having the following approximate characteristics:

$[\alpha]_D^{20} = -232°$ ($c = 0.64$ in $CHCl_3$)
UV spectrum in $CH_3OH$: end absorption
IR spectrum in $CH_2Cl_2$: see FIG. 3
IH.N.M.R. spectrum in $CDCl_3$, 90 MH$_z$ (Tetramethylsilane as internal standard): see FIG. 4
Formula: $C_{63}H_{115}N_{11}O_{12}$
and when in amorphous powder form a m.pt. of 150°–153° C. and obtainable by hydrogenating cyclosporin G as defined in claim 1.

6. The compound of claim 1 which is isocyclosporin G.

7. A process for the production of a compound of claim 1 which comprises,
(a) cultivating a cyclosporin G-producing strain of the fungal species Tolypocladium under aerobic conditions in the presence of a nutrient medium until a sufficient amount of cyclosporin G is produced and thereafter isolating cyclosporin G, or
(b) reducing cyclosporin G by catalytic hydrogenation to produce dihydrocyclosporin G, or
(c) rearranging cyclosporin G under acidic conditions to produce isocyclosporin G.

8. A pharmaceutical composition useful in treating chronic inflammations or immunosuppressant disorders comprising a therapeutically effective amount of a compound of claim 1 in association with a pharmaceutical carrier or diluent.

9. A method of treating chronic inflammations or immunosuppressant disorders in animals, which comprises administering a therapeutically effective amount of a compound of claim 1 to an animal in need of said treatment.

* * * * *